United States Patent [19]
Weiss

[11] Patent Number: 5,868,668
[45] Date of Patent: Feb. 9, 1999

[54] SURGICAL INSTRUMENT

[76] Inventor: Sol Weiss, 17144 Bullock St., Encino, Calif. 91316

[21] Appl. No.: 115,473

[22] Filed: Jul. 15, 1998

[51] Int. Cl.⁶ ........................................................ A61B 1/32
[52] U.S. Cl. ............................................ 600/224; 600/221
[58] Field of Search .................................. 600/219, 220, 600/221, 222, 223, 224, 225

[56] References Cited

U.S. PATENT DOCUMENTS

| | | | |
|---|---|---|---|
| 430,350 | 6/1890 | McCully et al. | 600/220 |
| 2,374,863 | 5/1945 | Guttman | 600/224 |
| 2,545,201 | 3/1951 | Gilbert | 600/220 |
| 4,385,626 | 5/1983 | Danz | 600/220 |
| 4,971,036 | 11/1990 | Collins | 600/220 |
| 5,063,908 | 11/1991 | Collins | 600/220 |
| 5,499,964 | 3/1996 | Beck et al. | 600/220 |

*Primary Examiner*—Paul J. Hirsch
*Attorney, Agent, or Firm*—Gerald L. Price

[57] ABSTRACT

A surgical instrument having a handle having a first blade fixed thereto and extending outwardly therefrom. A blade housing is pivotally mounted to the handle having a second blade fixed thereto spaced from the first blade and extending outwardly therefrom. A pair of levers are pivotally mounted to the handle, each of the levers having a blade normally disposed adjacent each other and between the first and second blades. The blade housing has an open area therethrough whereby, when the first blade is pivoted away from the second blade, the blades on the levers move apart from each other to a position generally vertical with respect to the first and second blades and a surgical instrument can be inserted through the open area between the spread apart blades.

16 Claims, 11 Drawing Sheets

SURGICAL INSTRUMENT

BACKGROUND OF THE INVENTION

1. Field of the Invention

The invention relates to surgical instruments; and, more particularly, to diagnostic and surgical instruments for use in abdominal, thoracic or vaginal and anal surgical procedures that may also include endoscopies.

2. Related Art

Certain surgical and diagnostic devices are known for examining vaginal and other cavities. For example, women of a certain age should have a diagnostic pap smear annually. Certain prior art devices, known as speculums, are used which consist of a pair of wide or broad blades, but such are uncomfortable to the patient, causing much discomfort.

Also, when such instruments are used in examining a body cavity, such as the vagina, a second instrument is inserted into the vagina through the speculum. Such an instrument is called a lateral vaginal retractor and is used to retract the vaginal side walls which normally obstruct the doctor's view into the patient's cervix. During a surgical procedure, the surgeon needs to insert a clamp, a source of lighting, a suctioning catheter, and irrigation tube through the speculum, thus further obstructing the surgeon's view of the cervix which might interfere with the surgical procedure being performed.

There is a need for a surgical and diagnostic instrument which eliminates the need for a lateral vaginal retractor during vaginal surgery. Such an instrument should be anatomically designed with a narrow oval shape in its closed position to allow it to be inserted comfortably into the patient's vagina without the discomfort generally associated with a conventional speculum. It should also allow the introduction of other instruments such as a light, an irrigation tube, etc. without obstructing the surgeon's view.

SUMMARY OF THE INVENTION

It is an object of this invention to provide a surgical and diagnostic instrument for examining a patient's body cavity, such as a vagina, eliminating the need for a lateral vagina retractor during surgery.

It is another object of this invention to carry out the foregoing object that is anatomically designed (four quadrant retraction allows the blades to be of less width producing a narrower instrumentation) to cause little if any discomfort to the patient.

It is still another object of this invention to provide a multi-bladed vaginal diagnostic and surgical instrument which is quickly and easily activated to expand the blades with slight rotation movement and little discomfort to the patient.

It is further an object of this invention to carry out the foregoing objects allowing easy insertion into the body cavity being examined without allowing the instrument to slip out of the body cavity during examination.

Such an instrument should allow a tenaculum and other diagnostic tools to be moved out of the area of view of the surgeon while carrying out diagnostic procedures.

These and other objects are preferably accomplished by providing a surgical instrument for spreading apart openings of natural orifices or surgically made openings to perform procedures on internal structures and/or organs of a patient. The instrument includes a main body portion having a plurality of blades that open to spread apart the area being examined so that a surgical tool can be inserted therein. The instrument can be eliminated from the area of view by allowing the surgical tool to pass up into a gate while maintaining the spread-apart condition of the area being examined. The blades can then be restored to their closed position after the tool is withdrawn. The gate may have a plurality of notches for accommodating differing surgical tools

DESCRIPTION OF THE PREFERRED EMBODIMENT

Figure 1:
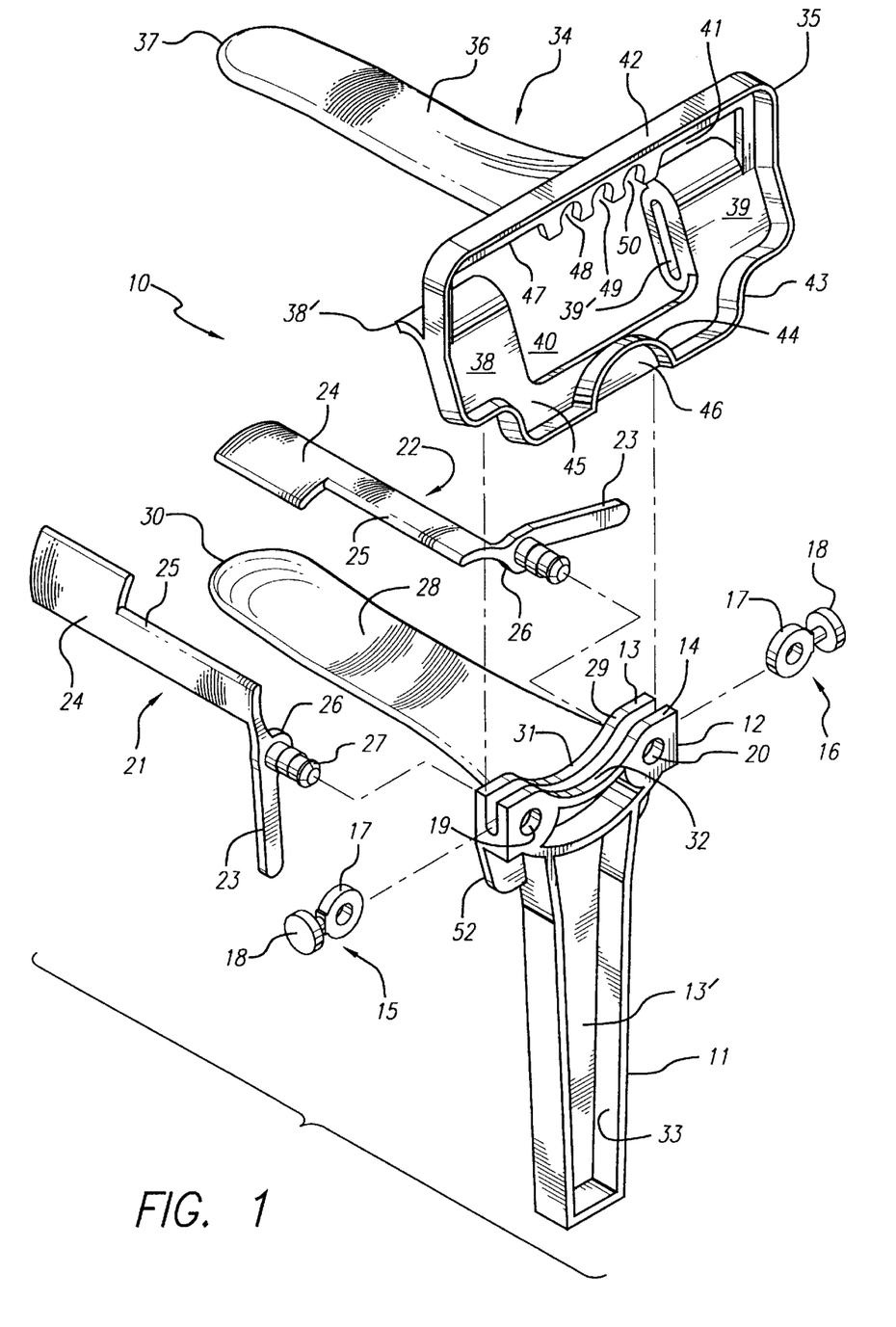
FIG. 1 is an exploded view of a surgical instrument in accordance with the teachings of the invention.

Referring now to FIG. 1, a surgical instrument 10 is shown having a handle 11 and an integral flanged portion 12 comprised of a pair of spaced flanges 13, 14 and a planar midsection 13'. A pair of knob and washer combinations 15, 16 are provided, each having an integral washer portion 17 and an integral knob portion 18. These combinations 15, 16 are adapted to be inserted between flanges 13, 14 aligned with apertures 19, 20, respectively (aligned apertures similar to 19, 20 are disposed in flange 13 and are not visible in FIG. 1).

A pair of blades 21, 22 are provided, one being the mirror image of the other. Thus, each blade 21, 22 has a lever portion 23 and an integral blade portion 24 extending generally normal to the axis of lever portion 23. Blade portions 24 are arcuate in cross-section and each has an elongated neck 25 on the upper portion thereto (away from its respective lever 23). The curvature of blade portion 24 of blade 21 is toward the curvature of blade portion 24 of blade 22. The neck 25 eliminate possible pinching of one's tissue since only a small area is needed to push the flesh aside during examination. The use of four quadrants of blades, as will be discussed, eliminates the need for wide blades. Only a little push of the flesh to the side is needed.

Each blade 21, 22 has a boss 26 at the intersection of its respective lever portion 23 and blade portion 24. A stepped 3-part pin 27 is integral with each boss 26 extending away from blade portion 24 toward apertures 19, 20.

A third blade 28, wider than blades 21, 22 and slightly curved in cross-section is integral with flange 13 and extends outwardly therefrom in a plane generally normal to the plane of handle 11 below the upper edge 29 of flange 13. Blade 28, at its forward end 30, is curved and depressed areas 31, 32 are provided in the middle of the upper edges of flanges 13, 14. The handle 11 may have a hollowed out interior 33 to save weight and costs of manufacture.

A blade assembly 34 is provided having a main body portion 35 and an integral fourth blade 36 extending therefrom lying in a plane generally normal to the plane of the main body portion 35. Blade 36 terminates at its forward end 37 in a curved end and is also slightly curved in cross-section.

Figures 3, 4:
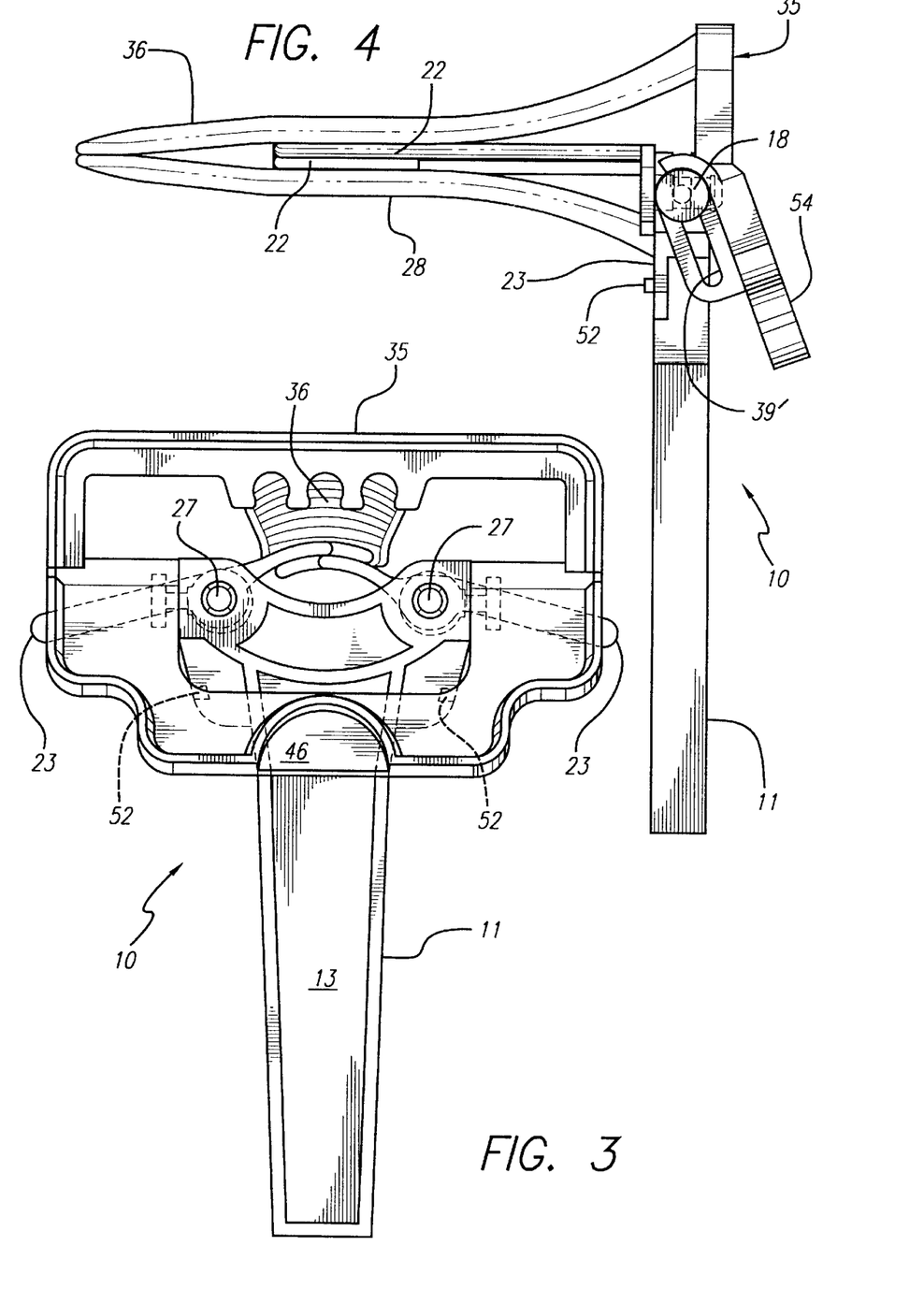
FIG. 3 is a rear view of the instrument of FIG. 2.
FIG. 4 is a side view of the instrument in FIG. 1.

Blades 21, 22, as seen in FIG. 4, are shorter than blades 28, 36.

Figure 2:
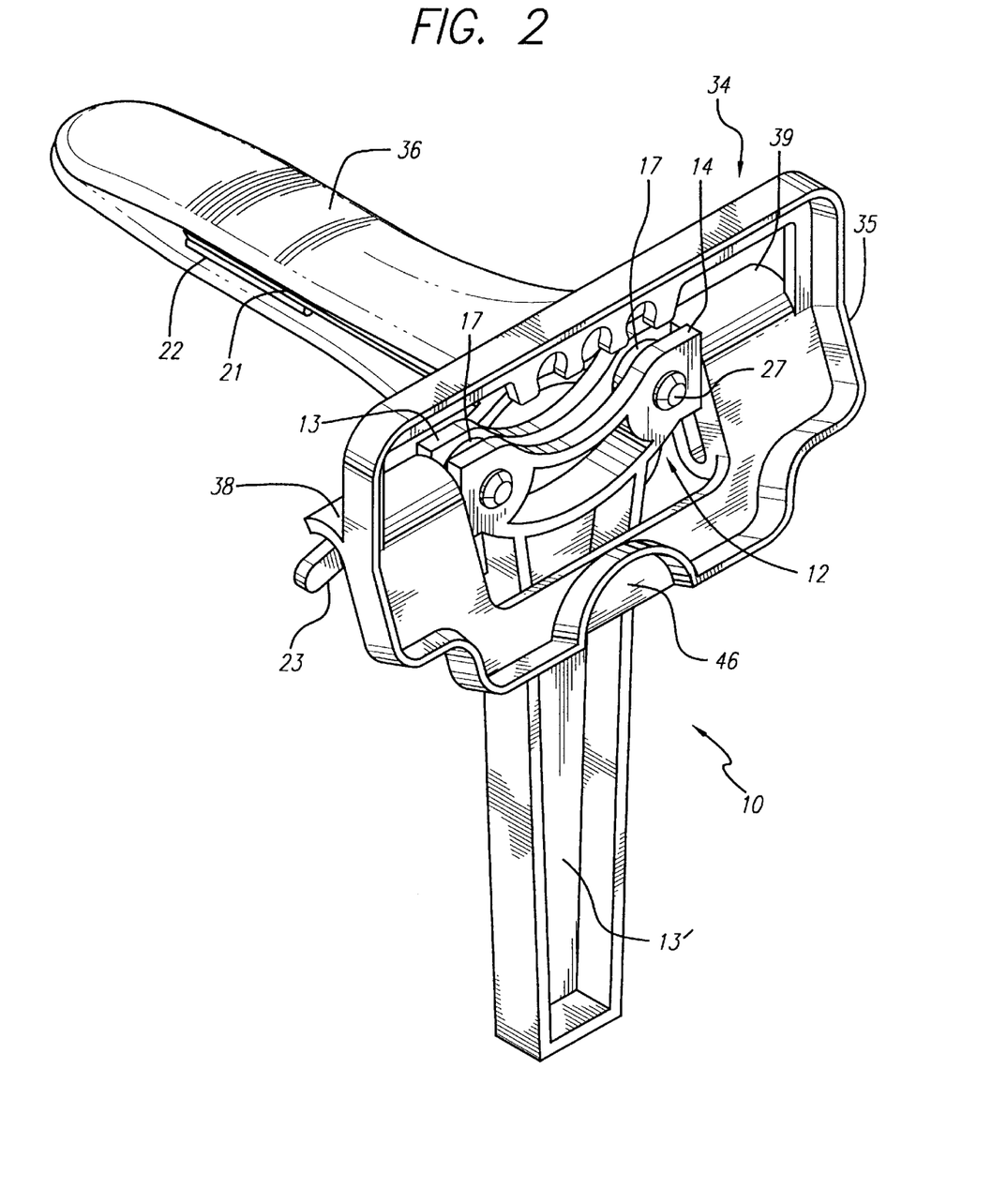
FIG. 2 is a perspective view of the assembled surgical instrument of FIG. 1.

Main body portion 35 is adapted to fit over flanged portion 12 (FIG. 2) and is generally rectangular with a pair of spaced inner curved walls 38, 39 flanged at top (see flange 38' in FIG. 1) forming a space 40 therebetween with an upper gap 41 formed between the upper rail 42 of main body portion 35 and the lower rail 43 thereof An oval opening or slot 39' is formed integral with each curved top flange 38'. Rail 43 has a raised flange portion 44 at generally the middle thereof and walls 38, 39 are interconnected by an inner partition wall 45. Walls 38, 39 are curved at their upper ends. A portion 46 of wall 45 is thus accessible below flange portion 44 to provide a thumb rest for instrument 10 as will be discussed.

Rail 42 includes a downwardly depending elongated flange 47 having a plurality of spaced notches 48 to 50 for reasons to be discussed. Although shown as grooves, tracks, or notches, notches 48 to 50 can have a variety of configuration, It can be seen by comparing FIGS. 1 and 2 that the main housing portion 35 of blade assembly 34 is mounted over flanged portion 12. The washers 17 of combinations 15, 16 are inserted between spaced flanges 13, 14. Stepped pins 27 are now inserted into the respective aligned apertures 19, 20 with levers 23 extending out of slots 39' (see FIG. 4) and thus accessible outside of blade assembly 34.

As seen in FIG. 3, additional safety locks may be provided in the form of a pair of ramps 52 on opposite sides of flange portion 12 (see also FIG. 4) for reasons to be discussed.

As seen in FIG. 4, the flanged portion 12 is at an angle with respect to handle 11 so that knobs 18 are retained within slots 39'. The lower portion 54 of main housing portion 35 is also angled as seen in FIG. 4.

Figure 5:
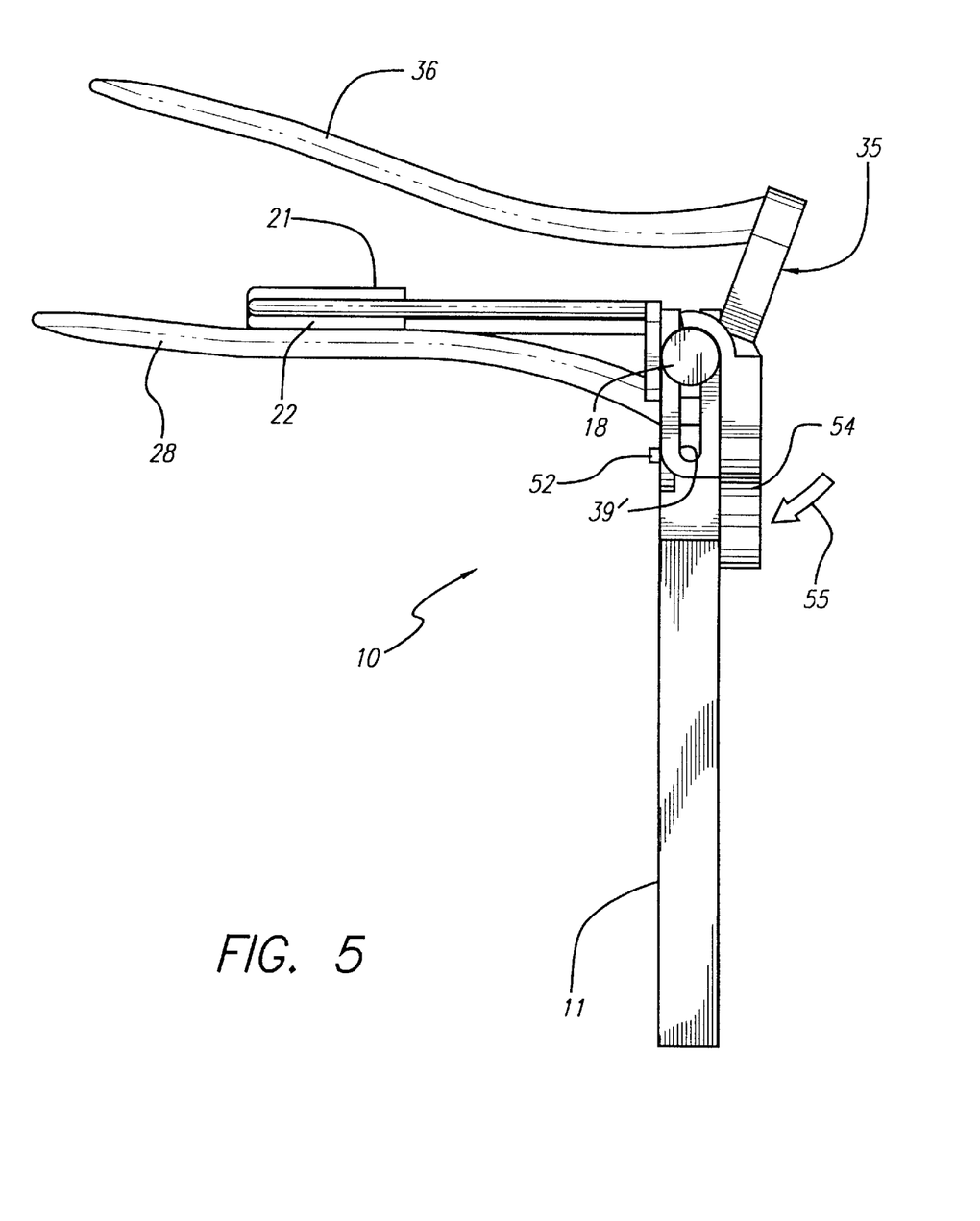
FIG. 5 is a view similar to FIG. 4 showing the blades in partial open position.

In operation, as seen in FIG. 5, pushing it at thumb rest 46 (not visible in FIG. 5—see FIG. 2) on lower portion 54 in the direction of arrow 55 raises blade 36. Continuing to push up on thumb rest 46 in the direction of arrow 55' raises blade 36 further with knob 18 moving down slot 39' to the FIG. 6 position.

Figures 6, 7:
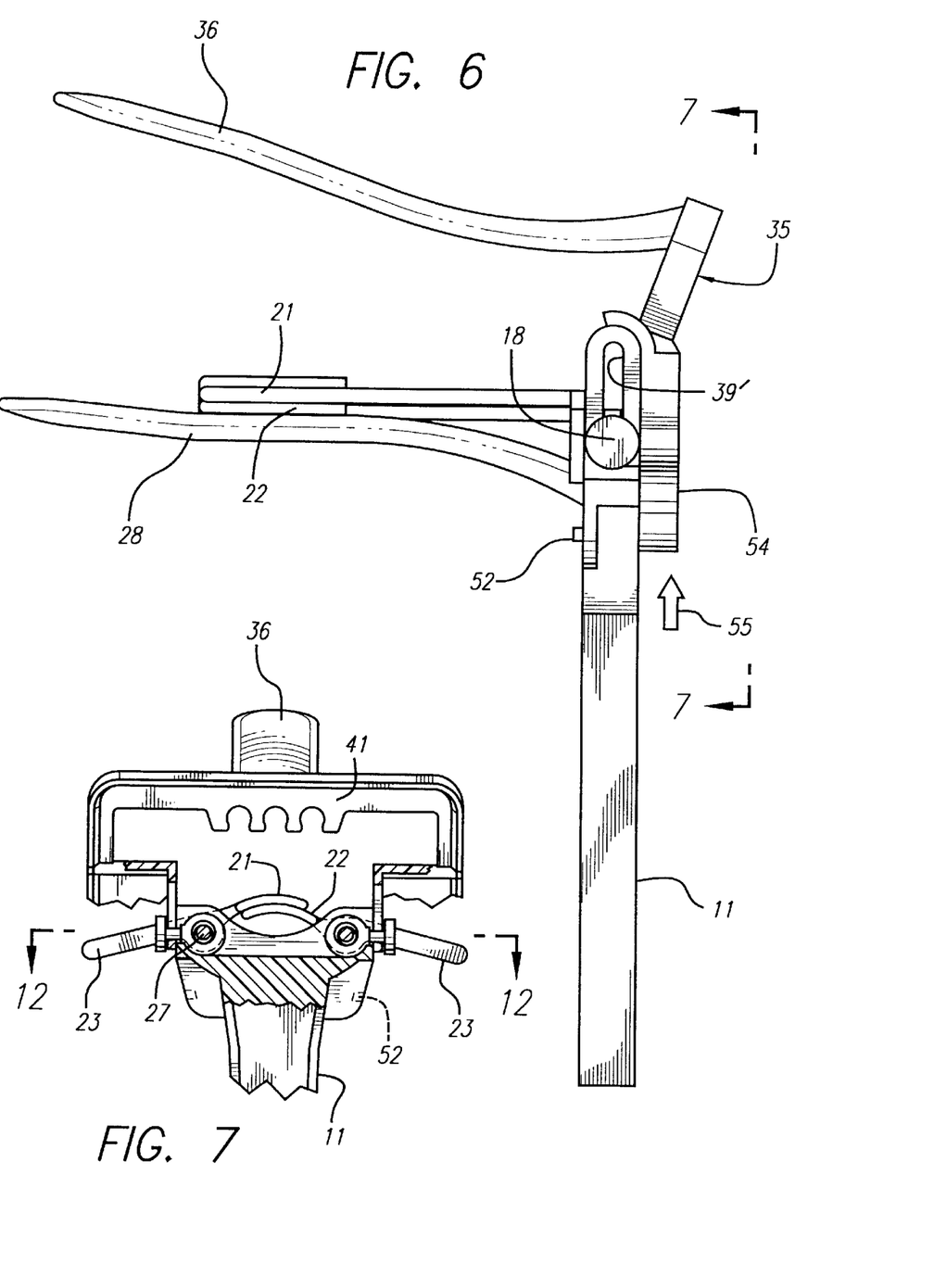
FIG. 6 is a view similar to FIG. 5 showing the top and bottom blades in full open position.
FIG. 7 is a view taken along lines 7—7 of FIG. 6.
Figures 8, 11:
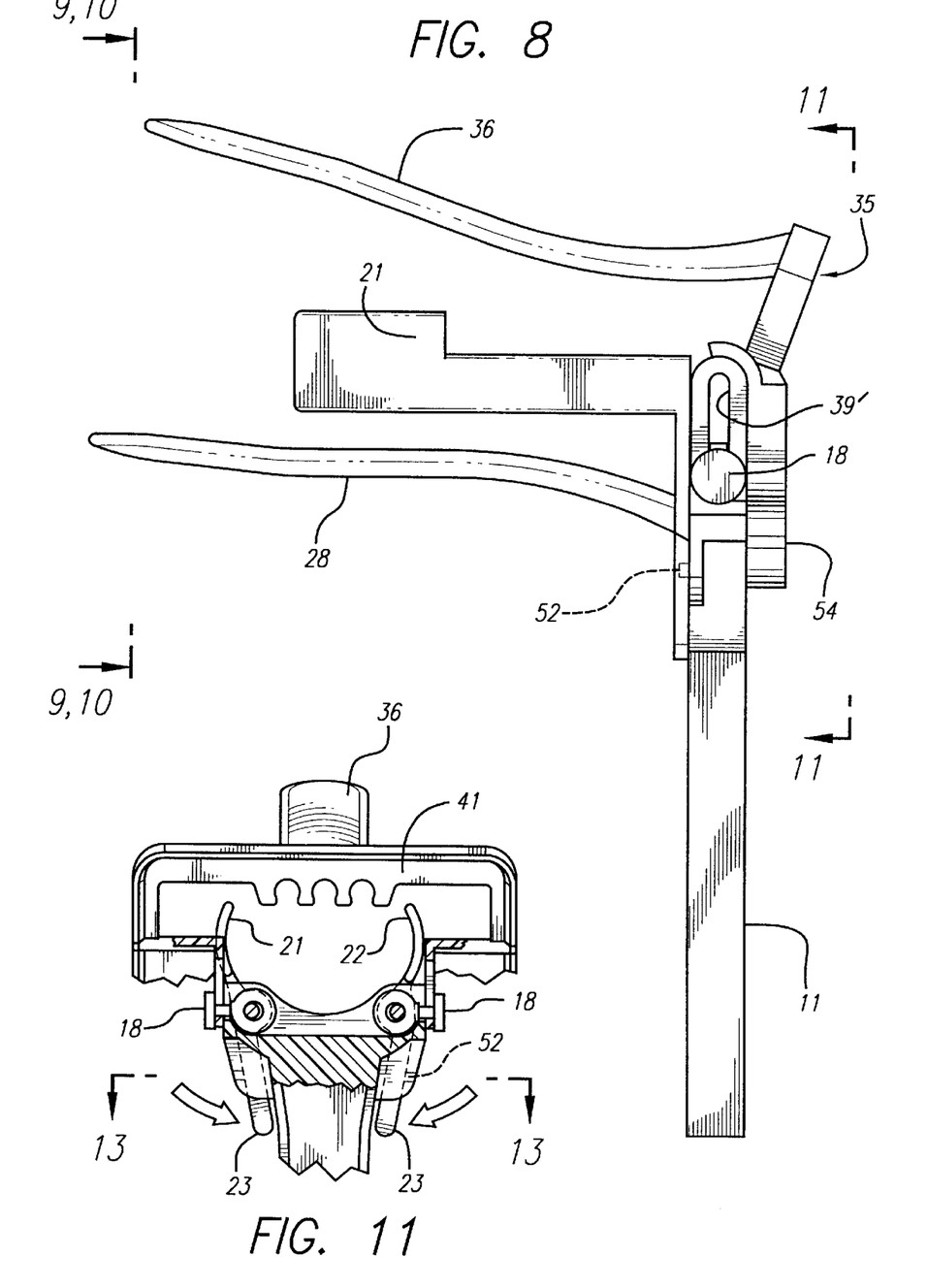
FIG. 8 is a view similar to FIG. 6 showing the side blades in open position.
FIG. 11 is a view taken along lines 11—11 of FIG. 8.
Figure 9:
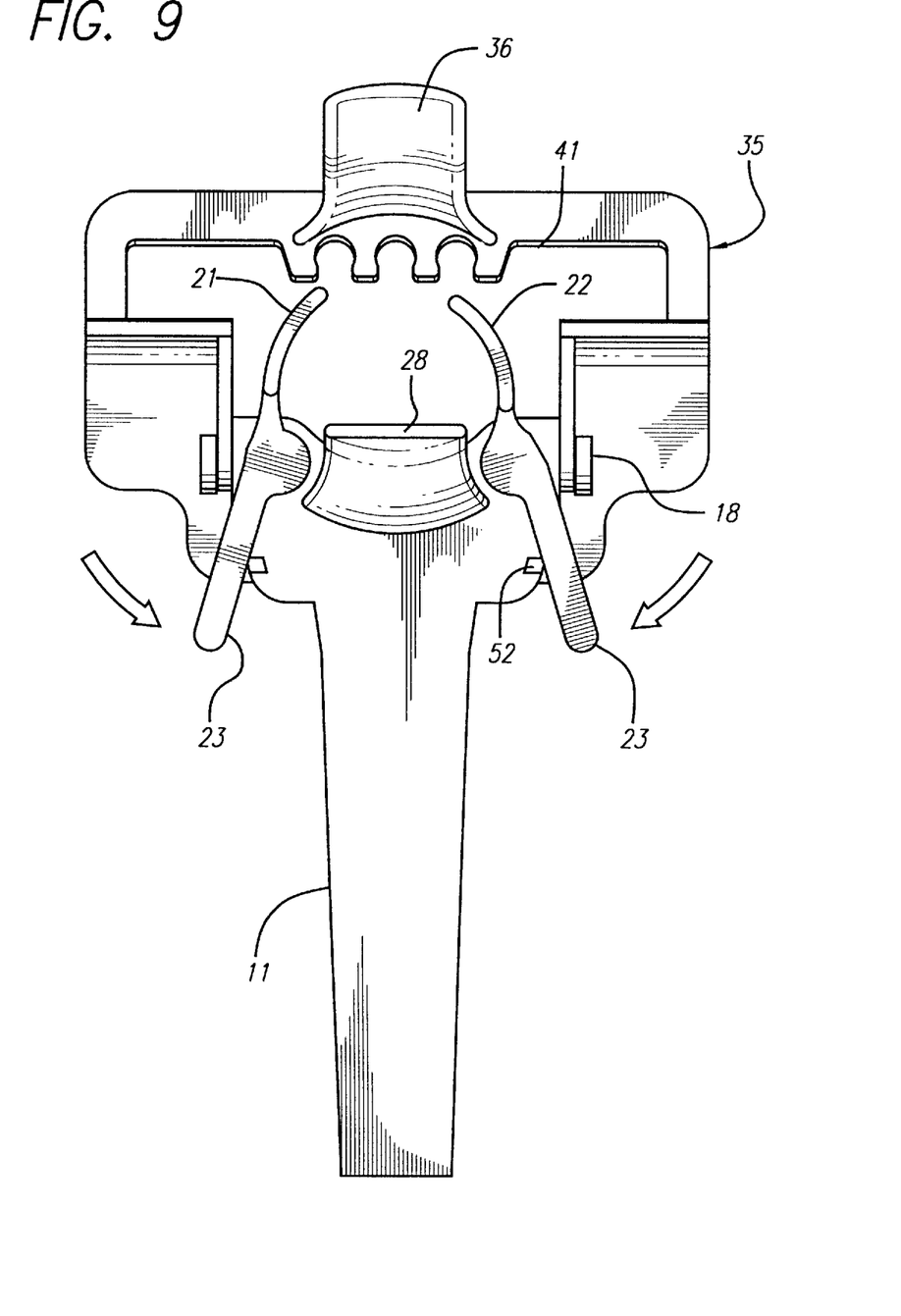
FIG. 9 is a an elevational view of the instruments of FIGS. 1 to 8 showing the arms moved to a downward position.
Figure 10:
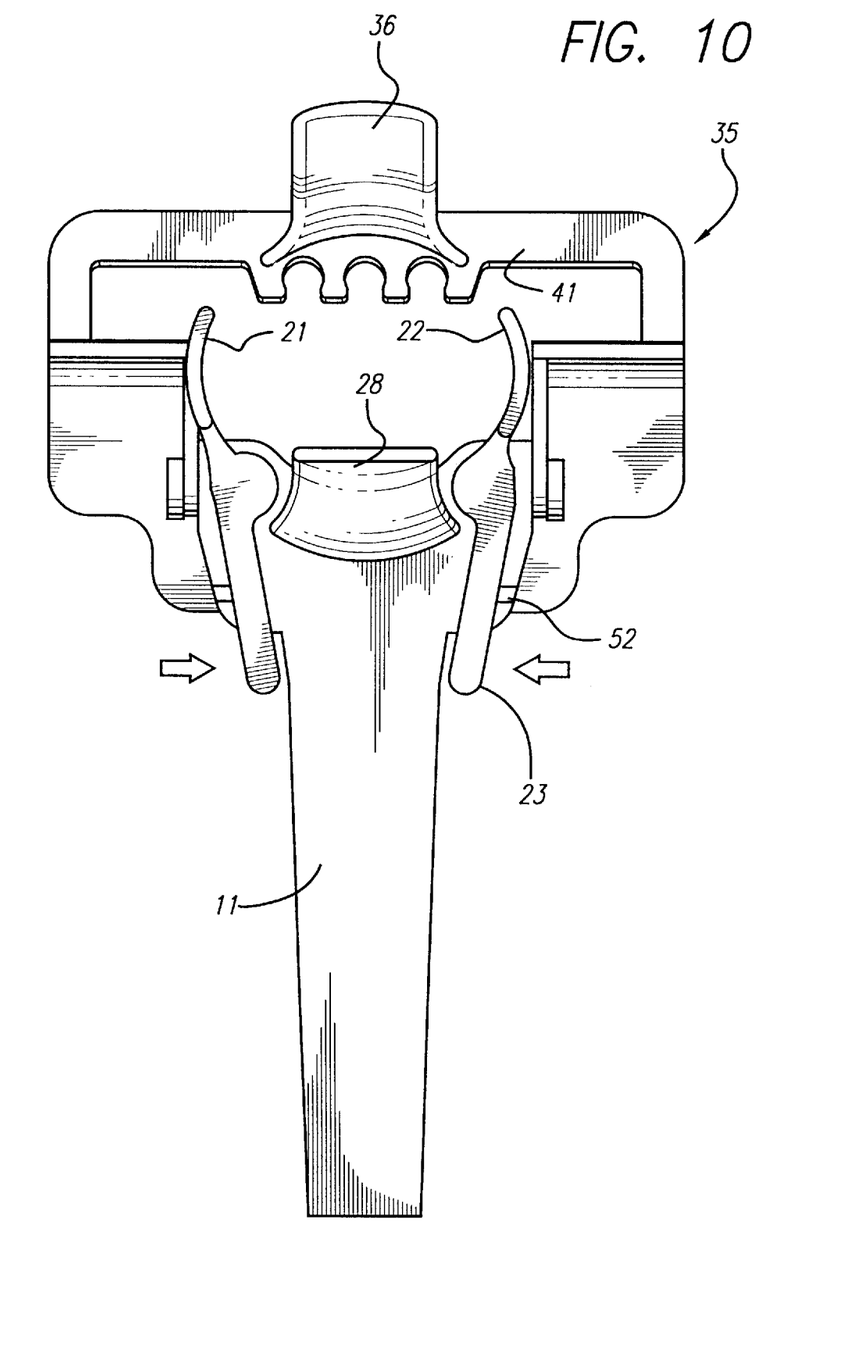
FIG. 10 is a view similar to FIG. 9 showing the arms in a final locked position.
Figure 13:
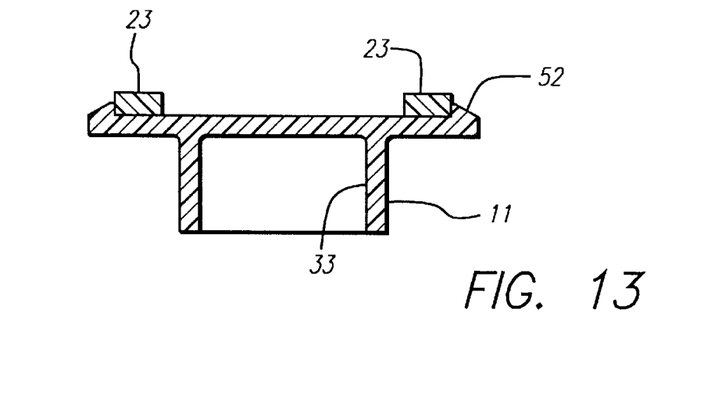
FIG. 13 is a view taken along lines 13—13 of FIG. 11.

At this time, as seen in FIG. 7, levers 23 can be pulled down raising blades 21, 22 to the position shown in FIG. 8. Levers 23 move downwardly over ramps 52 (FIG. 11) and over the ramps 52 to the FIG. 10 position thus locking the same therein as seen in FIG. 13. Thus, as seen in FIG. 11, levers 23 have been moved downwardly in the direction of the arrows to the locked position (see FIG. 9) shown forming a space between the curved blades 21, 22 (FIG. 11). The final position is shown in FIGS. 10 and 11.

Figure 12:
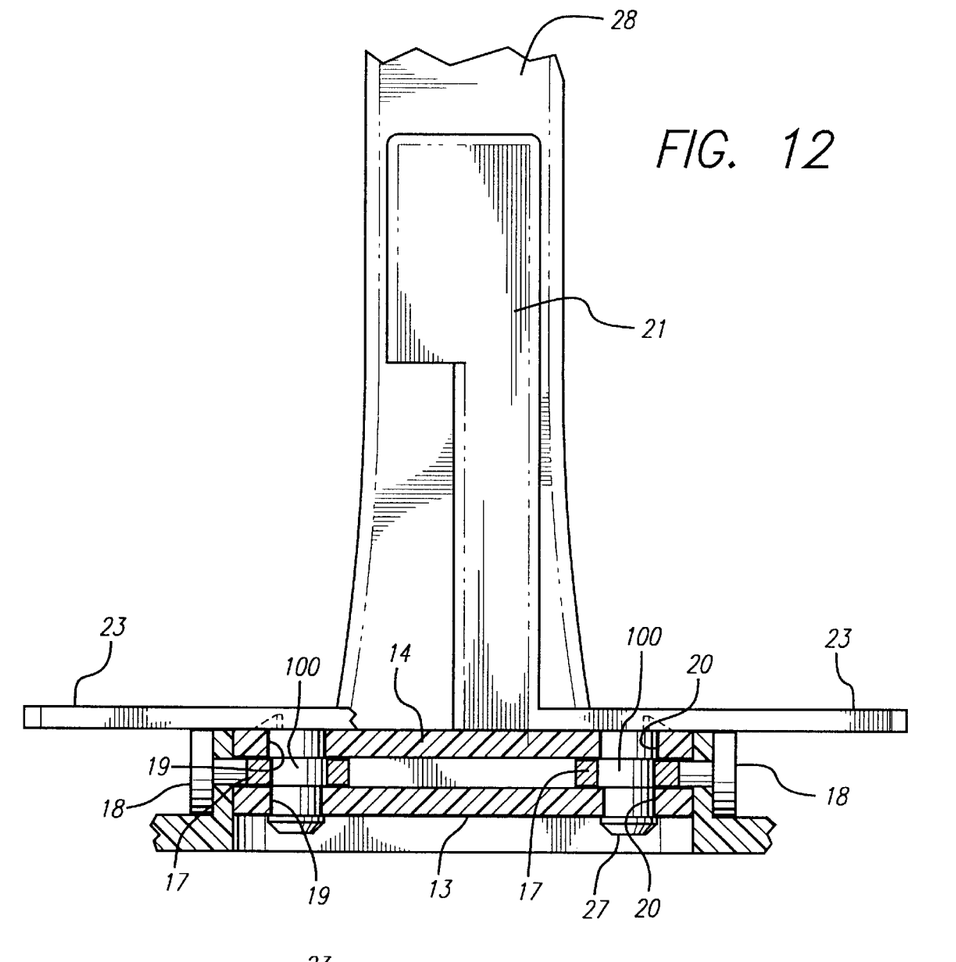
FIG. 12 is a view taken along lines 12—12 of FIG. 7.

As seen in FIG. 12, pins 27 extend through aligned apertures 19, 20 in flanges 13, 14 as previously discussed.

Pins 27 are stepped or not perfectly round such as having a non-round or spiraled midsection 100 so that, when the arms 23 are rotated downwardly, knobs 18 are pulled inwardly tightening the levers 23 thereby tightening blades 21, 22.

Figure 14:
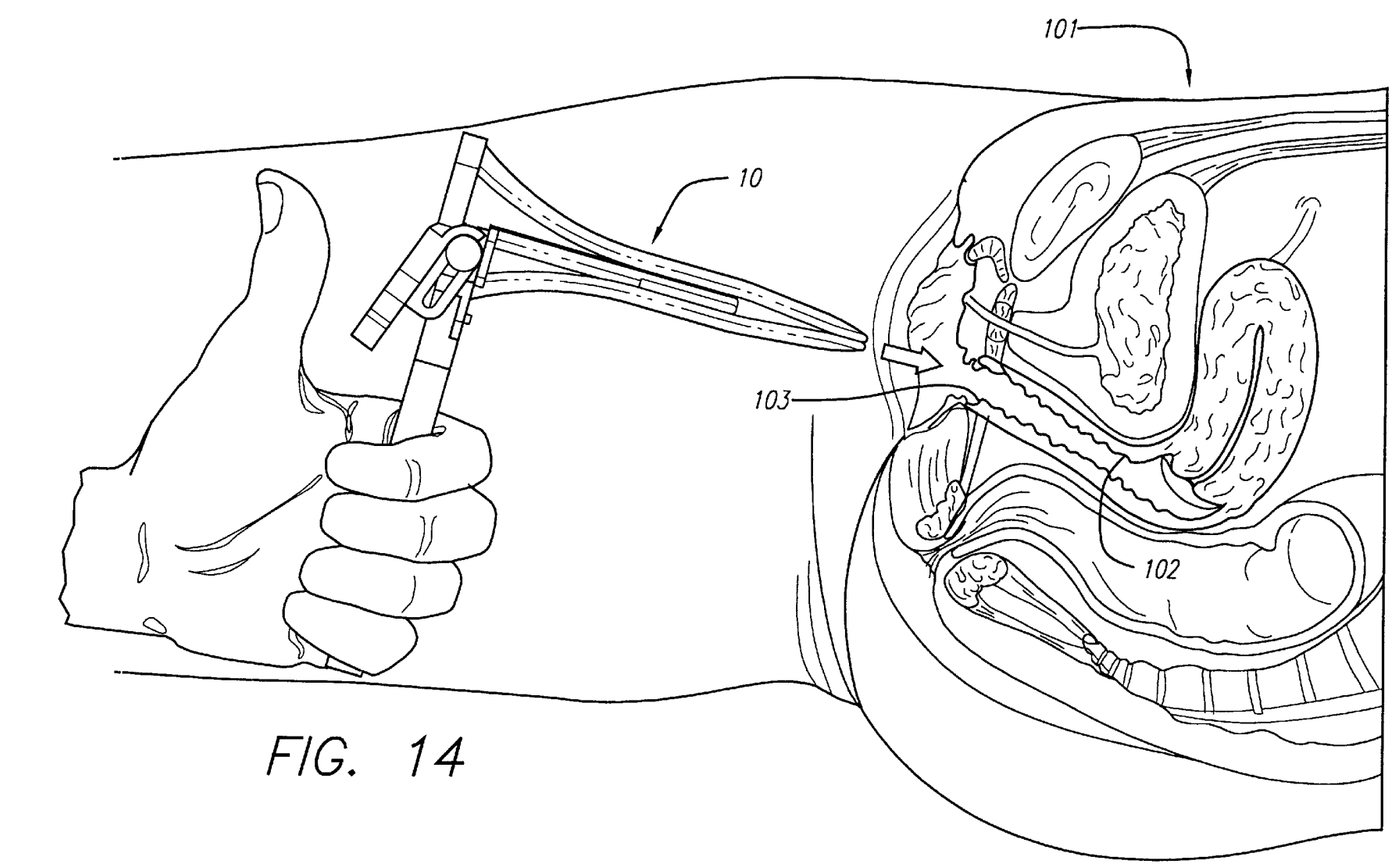
FIG. 14 is a perspective view illustrating the use of the instrument of FIGS. 1 to 13.
Figure 15:
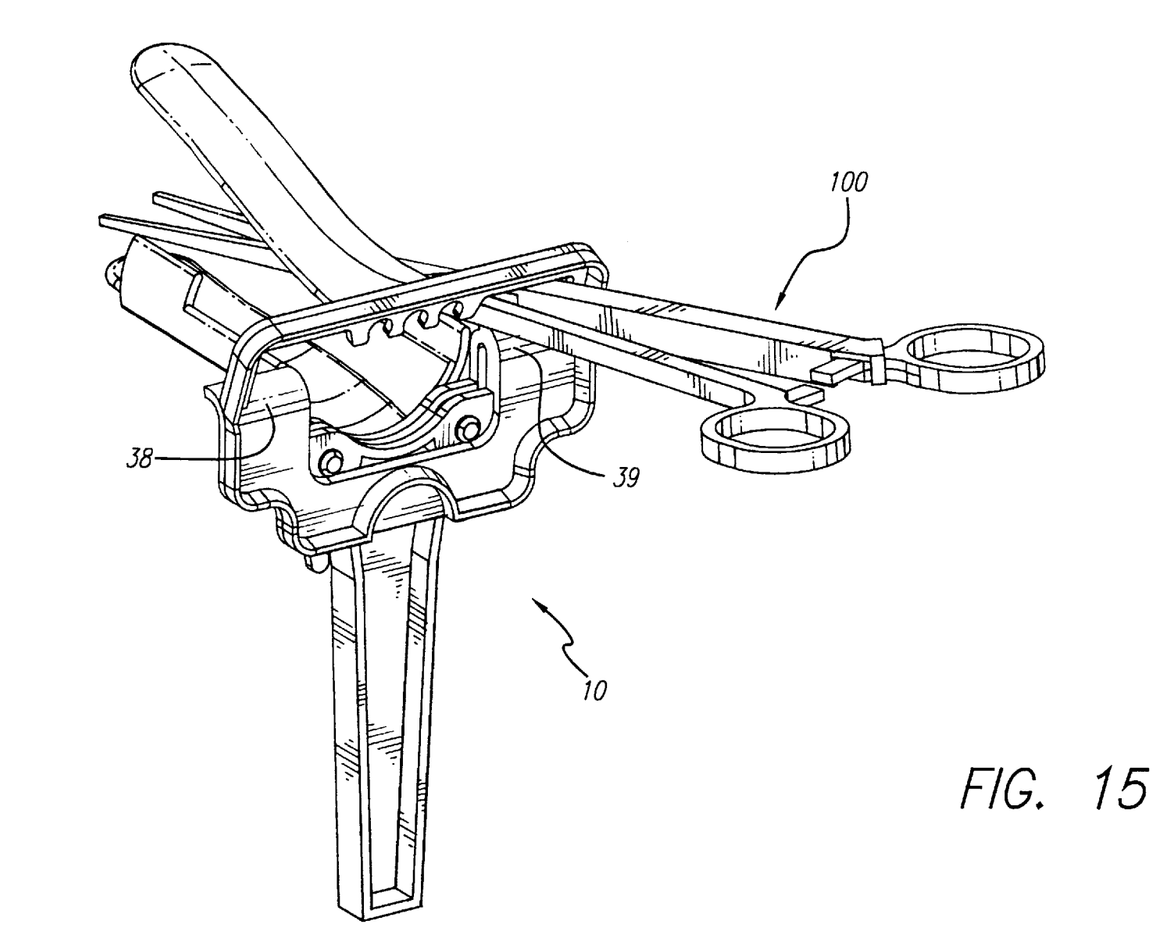
FIG. 15 is a perspective view of a conventional tenaculum used with the instrument of FIGS. 1 to 13.

The operation of instrument 10 will now be discussed. The abdomen 101 of a patient is shown in FIG. 14. Surgical instrument 10, which in the FIG. 4 position has a narrow oval configuration in cross-section, is shown as about to be inserted into the vagina 102 and about to be opened to spread apart the blades 21, 22, 28, 36 position as in FIGS. 5 and 6 to hold wide open the vaginal pouch 103. A conventional tenaculum 100 (see FIG. 15) is now inserted between the open blades of instrument 10 grasping the cervix of the uterus. The surgeon or doctor can then carry out his or her diagnostic and therapeutic procedures on the patient's pelvic organs. The instrument 10 can be moved off to the side allowing the tenaculum 100 to pass or go through the areas above flanges 38, 39 as seen in FIG. 15 as the instrument 10 is moved and tilted out of vision of the doctor. The areas each may be about ½" to 1" wide. This provides better visibility for diagnostic procedures and insertion of further instruments, if necessary and allow the tenaculum 100 to be bypassed by the instrument 10. That is, the open areas are not a barrier to the tenaculum 100 as the instrument 10 is moved off to the side and the tenaculum 100 is disposed in the areas on each side of notches 48 to 50. Other instruments, such as a light, not shown, may be disposed in any one of notches 48 to 50. No other prior art instruments shows multiple tracks for the purpose of providing for light and suction in such instruments.

There is thus disclosed a surgical instrument which is a four-way spreader useful in examining the body of a patient. The spreader holds open the area one desires to examine, such as the vaginal pouch leading to the uterus, and can be moved quickly and easily off to the side upon insertion of a conventional diagnostic tool, such as a tenaculum, to provide better visibility and maneuverability. The instrument can be made of any suitable materials, such as plastic.

It can be seen that there is disclosed a surgical and diagnostic instrument for examining body cavities of a patient, particularly women's vaginas.

Only one instrument is needed instead of two, thus reducing the cost associated with such a procedure which is of prime importance in this age of managed care. With one instrument and one operation, all four (4) quadrants of the instrument are spread to keep tissues from cascading into the incision site, and a more circular opening can be obtained. The four (4) blades also allow for less slippage from the organ while the instrument is expanded as compared with a conventional two-blade instrument.

Although particular sized blades are disclosed for examining a woman's vagina, the instrument can be used with different size blades for the following applications:

1. Vaginal
2. Rectal
3. Ear, nose, and pharyngeal
4. Laparoscopies
5. Abdominal and thoracic surgeries.

A fiberoptic cord may be attached to the instrument and disposed in any one of the notches 48 to 50 for additional lighting in the body canal. The notches and areas on each side of notches 48 to 50 allows one to position an irrigation tube and clamp outside of the surgical site, thus eliminating the obstruction encountered by current instruments as heretofore described.

It is further the scope of this invention to have the capability of making disposable, removable blades (different size blades for different procedures) with a stainless steel reusable handpiece. This will assist in preventing contamination between patients and thus will make these procedures safe to the patients in this age of HIV and hepatitis contagious diseases.

In conclusion, the diagnostic and surgical instrument as disclosed herein provides a single operation instrument with a four-way blade spread. All four blade quadrants are spread to keep tissues from cascading into the incision site. A more circular instrument opening is available. A variety of larger instrument openings are possible due to the lockable levers 23, 24 which may have been somewhat limited in prior instruments due to their housing. This is important for closed system surgeries. The instrument's gradual spread with handles allows better control of the instrument depth. Manual control allows for less slippage and a plurality of tubes may not be necessary to increase the size of openings.

The use of four blades allows for less slippage when expanding than two blades. The instrument's smaller housing on top thereof makes the instrument more adaptable to many uses. The curved housing blades allow for better placement of the instrument in surgeries and vaginal exams. The instrument disclosed herein allows the use of different shapes of blades as seen in other retractors for other types of surgical and/or examination procedures. The instrument herein is cheaper and easier to manufacture and assemble and thus reduces cost. It requires less steps than prior art devices for performing the procedure.

The instrument can be made entirely of any suitable materials, such as plastic material. Some of the uses of the instrument herein are:

Skin and subcutaneous tissue:
1. Foreign bodies
2. Lymph nodes
3. Ganglionectomy
4. Laparascopy and other abdominal surgery
5. Spinal (neurosurgical)
6. Neck surgeries
   a. Emergency (closed system)
   b. Permanent
7. Thoracotomy
   a. Emergency
   b. Elective
8. Facial procedures The instrument can be used for the following examinations:
1. Vaginal
2. Rectal
3. Ear and nasal and, possibly, pharyngeal Fiberoptic blades can be provided for deep lighting Although a particular embodiment of the invention is disclosed, variations thereof may occur to an artisan and the scope of the invention should only be limited by the scope of the appended claims.

I claim:

1. A surgical instrument for carrying out diagnostic and therapeutic procedures on the interior organs of the human body comprising:
   a handle having a pair of integral spaced flanges at the upper end thereof, said spaced flanges having a pair of spaced apertures therethrough, and a first blade fixed to said flanges extending outwardly therefrom;
   a flange housing mounted to said spaced flanges also having a second blade fixed thereto extending outwardly spaced from and above said first blade;
   a pair of levers, each of said levers having a pivot pin receivable in one of said apertures through said flanges pivotally mounting said levers to said flanges, and each of said levers having a blade integral therewith and extending outwardly therefrom, each of said blades mounted to said levers being disposed one above the other between said first and second blades and adapted to move from a first position lying in a plane generally parallel to the planes of said first and second blades when said first and second blades are disposed substantially adjacent each other and movable to a second position lying in generally a plane vertically disposed with respect to the planes of said first and second blades when the latter are moved apart;
   said flange housing having an opening therethrough for receiving a surgical instrument therethrough.

2. The instrument of claim 1 including a plurality of spaced notches on said flange housing above said opening.

3. The instrument of claim 1 including a pair of slots mounted in said opening on opposite sides thereof forming a space therebetween, and a plurality of spaced notches on said flange housing above said space.

4. The instrument of claim 3 including open areas provided in said flange housing on both sides of said notches above said slots.

5. The instrument of claim 3 wherein said pins extend through washers mounted between said spaced flanges, each of said washers having a knob portion integral therewith extending out of said slots, said knob portions being movable downwardly in said slots when said blades integral with said levers move from said first to said second positions.

6. The instrument of claim 5 wherein said pins are irregularly shaped in cross-section to tighten up in said apertures when said blades integral with said levers move from said first to said second position.

7. The instrument of claim 1 wherein the upper portion of said flange housing lies in a plane angled with respect to the plane of the lower portion thereof, said first blade extending from said upper portion.

8. The instrument of claim 7 including a thumb rest on said flange portion at the lower end thereof wherein pushing on said thumb rest pivots said first blade upwardly and away from said second blade.

9. The instrument of claim 1 including a pair of ramps mounted on opposite sides of said handle whereby, when said levers are moved downwardly thereby moving said respective blades mounted to said levers from the first to the second position, said levers ride over said ramps to a locked position to prevent slippage during surgical procedures.

10. The instrument of claim 1 wherein said first and second blades are curved in cross-section.

11. The instrument of claim 1 wherein said blades integral with said levers are curved in cross-section, each having a notch extending from its point of connection to its respective lever away therefrom terminating before the terminal end thereof.

12. The instrument of claim 1 wherein said handle is of stainless steel.

13. The instrument of claim 1 wherein said blades are of plastic.

14. A surgical instrument comprising:
   a handle having a first blade fixed thereto and extending outwardly therefrom;
   a blade housing pivotally mounted to said handle having a second blade fixed thereto spaced from said first blade and extending outwardly therefrom;
   a pair of levers pivotally mounted to said handle, each of said levers having a blade normally disposed adjacent each other and between first and second blades; and said blade housing having an open area therethrough whereby, when said first blade is pivoted away from said second blade, and said blades on said levers are seperated apart from each other to a position generally vertical with respect to said first and second blades, a surgical instrument can be inserted through said open area between said spread apart blades.

15. The instrument of claim 14 wherein said blades mounted to said levers can be locked in a position to prevent slippage during surgical procedures wherein said blades mounted to said levers are generally vertical with respect to said first and second blades.

16. The instrument of claim 14 wherein a plurality of spaced notches are provided on said blade housing above said open area.

* * * * *